US005466247A

United States Patent [19]
Scheiner et al.

[11] Patent Number: 5,466,247
[45] Date of Patent: Nov. 14, 1995

[54] SUBCUTANEOUS ELECTRODE FOR STIMULATING SKELETAL MUSCULATURE

[75] Inventors: Avram Scheiner, University Heights; Ernest B. Marsolais, Shaker Heights, both of Ohio

[73] Assignee: Case Western Reserve University, Cleveland, Ohio

[21] Appl. No.: 140,815

[22] Filed: Oct. 21, 1993

Related U.S. Application Data

[63] Continuation of Ser. No. 884,723, May 18, 1992, abandoned.

[51] Int. Cl.$^6$ ............................................. A61N 1/04
[52] U.S. Cl. .............................. 607/48; 607/116; 128/642
[58] Field of Search .............................. 128/642; 607/48, 607/115, 116, 119, 129

[56] References Cited

U.S. PATENT DOCUMENTS

| | | | |
|---|---|---|---|
| 4,287,896 | 9/1981 | Grigorov et al. | 128/786 |
| 4,291,707 | 9/1981 | Heilman et al. | 128/784 |
| 4,972,846 | 11/1990 | Owens et al. | 607/129 |
| 5,269,810 | 12/1993 | Hull et al. | 128/642 |

Primary Examiner—Stephen C. Pellegrino
Assistant Examiner—Michael Peffley
Attorney, Agent, or Firm—Calfee Halter & Griswold

[57] ABSTRACT

A subcutaneously implantable device is provided for either electrically stimulating skeletal musculature or sensing electrical potential at its surface without directly contacting the musculature. The implantable device comprises an electrode constructed from a single generally planar sheet of electrically conductive material and having a first surface adapted to face the skeletal musculature and an opposite surface adapted to face away from the skeletal musculature. A flexible casing covers at least a substantial portion of the opposite surface of the electrically conductive sheet. At least one electrical lead is attached at one end to the electrically conductive sheet and is attachable at an opposite end to an electrical current source. The generally planar electrically conductive sheet is preferably comprised of a noble metal, such as platinum, and has a surface area sufficiently large to distribute the charge required to stimulate the targeted muscle. The electrical leads are preferably constructed from lengths of stranded stainless steel wire which are coiled in helical fashion to increase their capacity for elongation.

17 Claims, 2 Drawing Sheets

# SUBCUTANEOUS ELECTRODE FOR STIMULATING SKELETAL MUSCULATURE

This is a continuation of application Ser. No. 07/884,723 filed on May 18, 1992 now abandoned.

TECHNICAL FIELD

The present invention relates generally to electrical stimulation devices and more particularly to a subcutaneously implantable electrode for either electrically stimulating skeletal musculature or sensing the local electrical potential at its surface.

BACKGROUND OF THE INVENTION

Functional electrical stimulation (FES) is a procedure whereby electricity is used to restore motor function in paralyzed or neurologically impaired patients. FES treatment of debilitated musculature in persons so afflicted has been found to improve the physical capacities of the person by at least partially restoring the function of the damaged muscles. By functional electrical stimulation, electrodes are used to excite musculature by either directly stimulating the muscle fiber or indirectly stimulating nerves which are physiologically connected to muscle fiber. The excited nerves serially discharge neurons which innervate groups of muscle fibers which contract in response thereto. In this manner, gross muscular tension may be caused by a series of excitation signals applied to numerous muscle fibers. The amount of muscle fiber which is stimulated by an FES system is referred to as the level of recruitment.

The manner in which electrodes in functional electrical stimulation systems transmit electrical pulses to the nerves depends upon the physical relationship of the electrodes and the nerve endings. The method of electrode attachment in turn depends on the type of electrode being used in the system. Several types of FES electrodes are known in the art, including (i) intraneural electrodes, (ii) cuff electrodes, (iii) intramuscular electrodes, (iv) surface electrodes, and (v) epimysial electrodes. Each of these types of electrodes is constructed and operates in a particular manner.

Intraneural electrodes are placed within the nerve a manner which actually penetrates the nerve to be stimulated, piercing the nerve in at least one point. Epineural electrodes are also employed to stimulate muscle controlling nerves but are attached directly to the outside of the nerve. Typically an uninsulated conductive portion of an intraneural electrode is placed within the nerve and transmits electrical signals directly to the nerve. Because intraneural electrodes are implanted directly within individual nerves, they are useful in controlling specific muscle fibers. Intraneural electrodes are implanted with precision to insure that the electrode pierces but does not damage the nerve in which it is implanted.

Cuff electrodes, also known as nerve cuffs, physically surround the nerves to which the electrical signals are to be sent. Typically, a cuff electrode has at least one section of conductive material which contacts an outer surface of the nerve. Electrical signals propagate from this conductive material to the nerve to effect contraction of the muscle to be stimulated. Nerve cuff electrodes have a variety of applications in that they may be attached to either nerves that stimulate single muscles or to nerve trunks with branches that are connected to several muscles.

Intramuscular electrodes are implanted within muscle fiber and typically consist of a coiled wire with a non-insulated tip which is located immediately adjacent to or near the nerves of the muscle to be stimulated. Because the electrodes are implanted within the muscle, the conductive areas of the electrodes are usually very small, often consisting of a wire or group of wires having bare ends. Although the wires are useful in controlling individual muscles because the electrical charge can be delivered to a specific areas, effective recruitment of groups of muscles over a larger area of implantation is often difficult to obtain.

Surface electrodes are electrodes which are typically attached to the surface of the skin near the muscle to be stimulated. To ensure consistency in operation, the location at which the electrodes are attached must be rather precise. Also, the surface electrodes must be held in place on the skin by adhesive which must be cleaned off thoroughly when the electrodes are removed from the skin. Surface electrodes require relatively high current as compared to implanted electrodes to successfully activate the nerve fibers that lead to muscle contraction. Moreover, the process of attaching and removing the electrodes is time consuming, messy, and difficult for many patients to perform themselves, requiring the assistance of another person, usually a trained clinician.

Epimysial electrodes are implantable electrodes which are mounted to the surface of the epimysium, which is a fibrous sheath which surrounds skeletal muscle. The epimysial electrodes are surgically implanted and typically sutured to the epimysium of the targeted muscle. The electrode must be located as close as possible to the motor point, which is the optimum point for stimulation, of the muscle to maximize the muscular response. In the case of large muscles in which the motor point may be located far from the surface of the muscle, stimulation of the motor point is difficult using epimysial electrodes. Failure to stimulate the motor point may only cause contraction of the fibers in the close vicinity of the electrode, resulting in insufficient contractions to restore functionality to the limb. Further increases in operational current to obtain greater recruitment may cause contraction of nearby non-targeted muscle fiber.

Each of the electrodes described above is directly or indirectly interfaced to either muscle fiber or muscular nerve endings, and each functions in a characteristic manner. None of the above described electrodes, however, provide an implantable electrode which does not directly penetrate or attach to the surface of muscle or muscle controlling nerves, need not be sutured into position, and which provides a conductive surface area large enough to stimulate the motor point of larger muscles within the body. The electrode of the present invention provides these features in a device which can be implanted in a safe, easy and reversible manner, while at the same time providing a long lifetime of highly consistent and predictable performance.

SUMMARY OF THE INVENTION

The present invention provides a functional electrical stimulation device which also has applications as a sensing device, as well as a simple method of subcutaneously implanting the device in a patient on an outpatient basis. The device may also be easily removed from the body. The device includes an electrode which has a relatively large conductive surface area capable of supporting electrical current sufficient for recruiting a large number of muscle fibers. The device also includes a pair of electrical leads which provide the means by which electrical current is supplied to the electrode.

The electrode is implanted under the skin between the fatty layer and the cural or deep fascia which lies adjacent the muscle fiber to be stimulated. The electrode comprises an electrically conductive sheet disposed between upper and lower electrically insulative layers. A layer of fabric mesh is located between the electrically conductive sheet and the lower insulative layer. The electrically conductive sheet and the mesh fabric are secured between the upper and lower insulative layers by a medical grade epoxy.

The electrically conductive sheet is constructed from a noble metal such as platinum. Materials such as platinum are relatively flexible, tend to resist corrosion and provide high electrical conductivity and charge capacitance properties. The surface area of the platinum sheet is sufficiently large so as to distribute the electrical current required for acceptable levels of recruitment while maintaining a low charge density.

The electrically insulative layers are comprised of sheets of nonconductive and biocompatible material cut into elongated oval shapes. The upper layer entirely covers the electrically conductive sheet to insulate any electrical charge on the electrically conductive sheet from the pain receptors which are located near the patient's skin. The lower layer is provided with one or more openings the area of which is slightly smaller than the surface area of the electrically conductive sheet. The opening or openings provide the means by which electrical charge on the electrically conductive sheet stimulates muscle fiber.

The layer of fabric mesh is disposed between the lower electrically insulative layer and the electrically conductive sheet. The fabric mesh covers the electrically conductive sheet to maintain its position within the electrode. The mesh is constructed from a synthetic material which permits electrical charge to pass therethrough.

Electrical current is provided to the platinum sheet by means of the electrical leads which are constructed from flexible wires helically wrapped around a flexible core. The wires are electrically connected to the platinum sheet by spot welding. A portion of the helically wrapped wire and core arrangement is further formed into a coil, thereby forming a compound helix which increases the flexibility and elongation of the leads.

The electrical stimulation device comprising the electrode and at least a portion of the leads may be easily implanted subcutaneously within a patient by first making a small incision in the skin of the patient in close proximity to the musculature desired to be stimulated. Using a blunt instrument, a cavity is formed between the fatty layer and the cural or deep fascia. The electrode is inserted and deposited within this cavity. The electrode need not be sutured into position because minor movement of the electrode with respect to the nerves or muscle fiber to be stimulated is tolerated.

DETAILED DESCRIPTION OF THE PREFERRED EMBODIMENT

Figure 1:
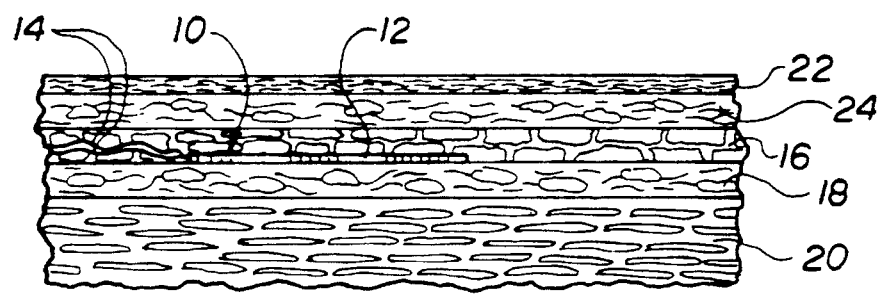
FIG. 1 is a perspective view of an electrical stimulation device constructed according to the principles of the present invention, shown implanted subcutaneously.

Referring now to the drawings, a functional electrical stimulation (FES) device 10 and an electrode 12 for use therein are shown in FIG. 1. The electrical stimulation device 10 is shown subcutaneously implanted within a patient. The device 10 comprises the electrode 12 and a pair of electrical leads 14 which provide the means by which electrical current is supplied from a separate current source to the electrode 12. The electrode 12 is implanted between a fatty layer 16 and the cural or deep fascia 18 which is a layer of fibrous tissue adjacent the muscle fiber 20 to be stimulated. Because the electrode 12 is implanted below both the skin 22 and the tela or superficial fascia 24, the electrode is insulated from impact or compressive forces which are applied to the skin 22 during daily activities of the patient into which the device 10 is implanted.

The electrode 12 of the present invention may also be used as a sensing device for sensing the local electrical potential at its surface. In such an application, the electrical leads 14 would provide the means to transmit the sensed electrical potential from the electrode 12 to an external apparatus for analyzing the signals.

Figure 2:
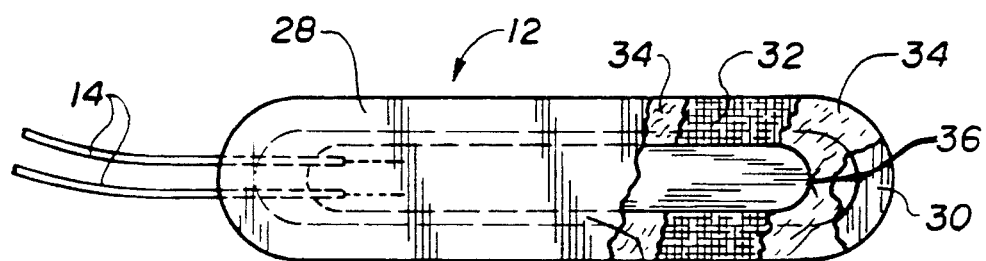
FIG. 2 is a plan view of the electrode of the device of FIG. 1.
Figure 3:
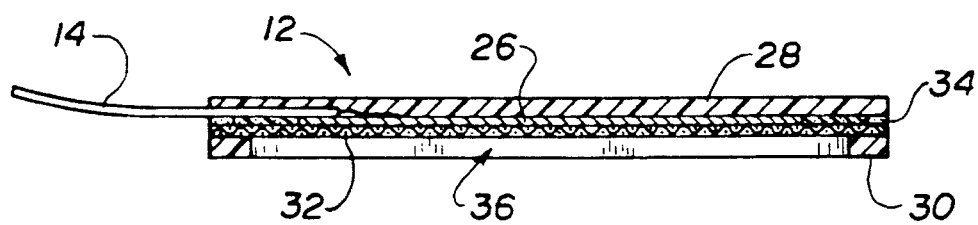
FIG. 3 is a cross sectional view of the electrode of FIG. 2.

The electrode 12 is further illustrated in FIGS. 2 and 3. The electrode 12 comprises an electrically conductive sheet 26 sandwiched between upper and lower electrically insulative layers 28 and 30, respectively. As used herein, "upper" shall define the side of any surface in the device which faces toward the skin 22 of the patient, and "lower" shall define the side of any surface in the device which faces toward the muscle fiber 20 to be stimulated. A layer of mesh fabric 32 is disposed between the lower surface of the electrically conductive sheet 26 and the upper surface of the lower electrically insulative layer 30, the purpose of which will be described later. The electrically conductive sheet 26 and the mesh fabric 32 are secured between the upper and lower insulative layers 28, 30 by a medical grade epoxy 34.

The electrically conductive sheet 26 is constructed from platinum in the preferred embodiment, although other materials are contemplated which (i) are relatively flexible, (ii) tend to resist corrosion and (iii) provide high electrical conductivity and charge capacitance properties. The material should be somewhat flexible to permit bending without breaking. Corrosion resistance is important because of the conditions under which the electrode operates, namely, under the influence of an electric charge and in a subcutaneous environment. Oxide coatings may be used to cover a portion of the surface area of the electrode to further reduce corrosion. The material must also be highly electrically conductive to efficiently conduct electricity from the electrical leads 14 to the nerve or muscle to be stimulated, or to conduct sensed electrical potential to an external analyzing apparatus. A high charge capacitance is required to permit relatively large charge to pass over the electrode-tissue interface. Noble metals such as platinum provide these qualities and are therefore suitable for constructing the electrically conductive sheet 26. Of course, other electrically conductive, biocompatible materials may be used to construct the conductive sheet 26. In the preferred embodiment, the platinum forming the electrically conductive sheet 26 has a thickness of about 0.025 mm, and provides an exposed surface area of around 25 mm×4 mm, or approximately 100 mm$^2$.

The exposed conductive surface area of about 100 mm$^2$ insures that the conductive sheet 26 will withstand a relatively large current while at the same time maintaining a low charge density. A relatively large current is required to obtain acceptable levels of recruitment, especially on larger muscles, such as the hamstring, quadriceps, and erector spinae muscles. A low charge density is necessary to prevent tissue damage and corrosion of the conductive sheet 26. It has been found that in the case of platinum, a charge density of less than 0.25 microcoulomb per square millimeter (0.25 µC/mm$^2$) will prevent such tissue damage and conductive sheet corrosion, although this allowable charge density will vary with the type of material used to construct the conductive sheet. Because sufficient recruitment requires currents on the order of 100 milliamps, the exposed surface area of the conductive sheet 26 must be at least 100 mm$^2$ to maintain the charge density at a maximum of 0.25 µC/mm$^2$. This relatively large surface area provides the capability to effectively stimulate the larger muscles of the body with less current than is typically required of a surface electrode because the subcutaneous electrode 12 is located closer to the motor point of the muscle.

The electrically insulative layers 28, 30 are comprised of sheets of a nonconductive and biocompatible silicone elastomer sheeting, such as medical grade SILASTIC®, which is a registered trademark of Dow Corning Corporation of Midland, Mich. for a multipurpose sealant. Each of the layers 28, 30 is cut into an elongated oval shape having planar dimensions of about 10 mm×40 mm and a thickness of approximately 0.12 mm to 0.13 mm. The upper layer of SILASTIC® 28 covers the entire upper surface of the electrically conductive sheet 26. In this manners electrical charge on the electrically conductive sheet 26 is insulated from pain receptors which are located near the skin. The lower layer of SILASTIC® 30 is provided with an aperture or opening 36 which defines the exposed area of the electrically conductive sheet. It is of course contemplated that more than one opening may be provided. The total surface area of the electrically conductive sheet 26 is slightly larger than the opening 36. The opening 36 provides the means by which electrical charge on the electrically conductive sheet 26 indirectly stimulates muscle fiber through nerve excitation.

The layer of fabric mesh 32 is disposed between the lower electrically insulative layer 30 and the electrically conductive sheet 26. The fabric mesh 32 covers the conductive sheet 26 and the entire upper surface of the lower SILASTIC® insulative layer 30 to maintain the position of the electrically conductive sheet within the electrode 12. The fabric mesh 32 is comprised of a synthetic material which will permit electrical charge to pass therethrough, and in the preferred embodiment is constructed from Dacron®, which is a registered trademark of Dow Corning Corporation for a synthetic polyester textile fiber (polyethyleneterephthalate). Of course, other biocompatible materials besides SILASTIC® and Dacron® may be used to construct the fabric mesh 32 and the insulative layers 28, 30.

The platinum sheet 26 and the Dacron® mesh 32 are secured within the upper and lower SILASTIC® layers 28, 30 by a nonconductive and biocompatible epoxy, such as medical grade liquid SILASTIC®. The completed electrode 12 thereby provides a compact, biocompatible package which lends itself to easy implantation within a patient.

Figure 2A:
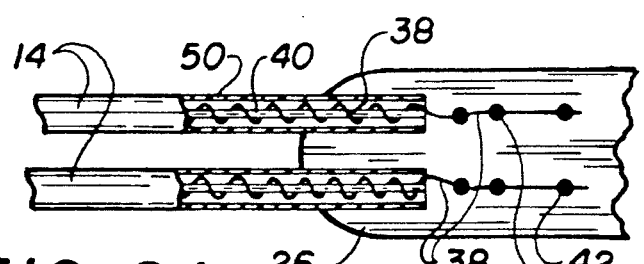
FIG. 2A is an expanded view of a portion of the electrode of FIG. 2.

Electrical current is provided to the platinum sheet 26 by means of the electrical leads 14. The leads 14 may be constructed from any type of flexible wire-like conductive material, such as cobalt alloys, but in the preferred embodiment are constructed from a pair of 30 AWG stranded stainless steel wires 38 (see FIG. 2A). Stainless steel is biocompatible, has sufficient hardness and strengths has a relatively low resistivity, and can be reliably drawn as fine as 20 µm in diameter. Preferably, the stainless wire is TEFLON® coated. TEFLON® is a registered trademark for a waxy, opaque material, polytetrafluoroethylene (PTFE), used as a coating to prevent sticking. The wires 38 are wrapped around a core 40, which may be constructed from a flexible and biocompatible material such as polypropylene, for example, PROLENE®, a trademark of Ethicon Inc. As illustrated in FIG. 2A, the wires 38 are electrically connected to the platinum sheet 26 by spot welding. In the preferred embodiment, three spot welds 42 are used to secure the wires 38 to the upper surface of the platinum sheet 26.

Although a pair of leads is shown in the Figures, the present invention may be implemented using a single lead. Employing two leads, however, provides several advantages. First, should one of the leads 14 fail, the other lead remains capable of delivering electrical current to the conductive sheet 26. In addition, utilization of a pair of leads facilitates electrical continuity testing. By placing a continuity tester, such as an ohmmeter, across the leads, the continuity of the electrical path between the pair of leads and the conductive sheet may be easily verified. Moreover, should one of the leads begin to corrode, the other lead will conduct more current, which will slow the corrosion process.

Figure 4:
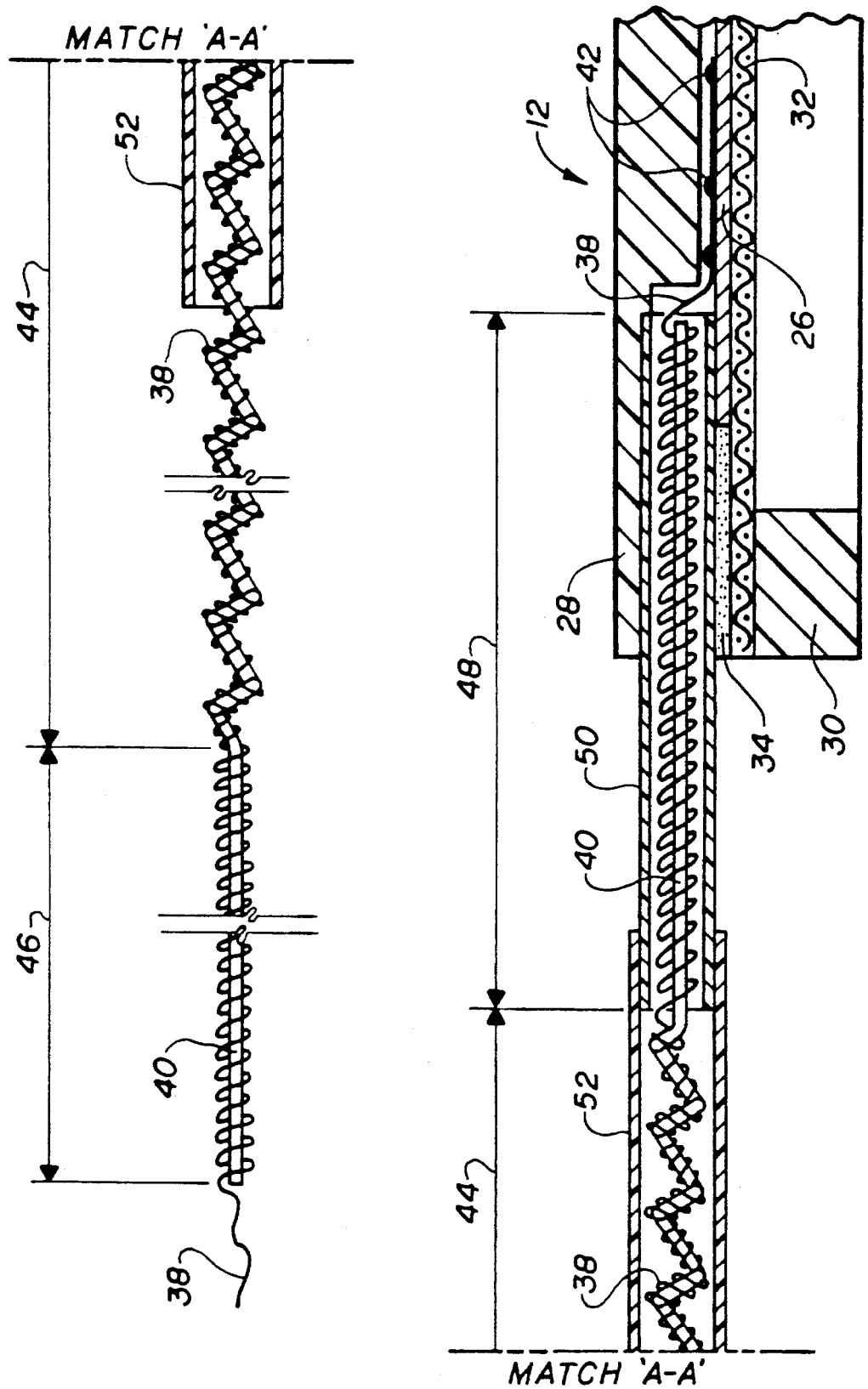
FIG. 4 is a side view of the device of FIG. 1.

The construction of the electrical leads 14 is further illustrated in FIG. 4. Extending beyond the area of the spot welds 42, the lengths of stranded wires 38 are wrapped in helical fashion around the PROLENE® core 40. The length of the leads 14 comprises (i) a first section 48 of wires 38 helically wrapped around the core 40, (ii) a second section 44 wherein the helically wrapped core and wire arrangement is itself formed in a helical coil and (iii) a third section 46, similar to the first section 48, wherein the wires 38 are helically wrapped around the core 40.

The first section 48 of the length of the leads 14 is covered by a protective flexible sleeve 50. The sleeve 50 may be constructed of 0.5 mm diameter SILASTIC® tubing, and provides stress relief for the covered portion of the leads 14. Optimally, additional stress relief may be provided by securing the sleeve 50 to the electrode 12 by means of the medical grade epoxy 34. The sleeve 50 also prevents this portion of the leads 14 from kinking. Absent the sleeve 50, the relatively compliant leads 14 would tend to twist or kink at the point at which the leads extend from the electrode 12.

The compound helical configuration of the second section 44 of the leads compounds the elasticity of this portion of the leads. Thus, this section 44 of the leads permits the leads to be elongated, through bending of the patient or tugging at the leads, so that the electrode 12 maintains its position near the nerve or musculature to be stimulated. A portion of the second section 44 is covered by a protective flexible sleeve 52. The sleeve 52 may be constructed of 0.76 mm diameter SILASTIC® tubing, and, like the sleeve 50, provides stress relief for the leads 14 as well as prevents the leads 14 from kinking.

The third section 46 of the leads is constructed similarly to the first section in the preferred embodiment, except that the third section is not covered by a protective sleeve. It is contemplated, however, that the entire length of the leads be covered by a protective sleeve. The length of the third section of the leads varies by application. If an electrical current source is implanted within the patient, the end of the third section opposite the second section would be attached to this current source or leads extending therefrom within the body of the patient. If, however, an external electric current source is utilized, the third section will pass through the surface of the skin and will be attached to the current source external to the body. Although the system 10 is adapted to be attached to an electrical current source, the current source forms no part of the present invention and will thereby not be described in further details as electrical current sources for electrodes are commonly known in the art.

The manner of applying electrical current to electrodes in musculature systems varies with the type of system and the musculature targeted for stimulation. The following electrical excitation cycle, however, has provided sufficient levels of recruitment in patients in which the electrode 12 has been implanted, by stimulating nerves which in turn fire to effectively stimulate the muscle. A series of alternating positive and negative current pulses, having an amplitude of around 100 milliamps, are applied to the electrode 12, followed by a rest period. In one of the preferred excitation cycles, operating at 50 Hz, negative current is applied for 250 μsec, followed by positive current for 250 μsec, followed by 19.5 msec wherein no current is applied. This cycle is performed fifty times during the first second of time, and followed by several seconds of rest. A similar excitation cycle can be operated at 20 Hz. In this case, negative current would be applied for 250 μsec, followed by positive current for 250 μsec, followed by 49.5 msec wherein no current is applied. This cycle is performed twenty times during the first second of time, and followed by several seconds of rest. The two excitation patterns described above are only made by way of example, and other methods of electrode excitation are contemplated by the present invention. Moreover, muscle fiber may be stimulated directly with the electrode 12 but the threshold for such direct stimulation is 5–10 times higher than for stimulating the nerve which innervates the muscle.

The electrical stimulation system 10 thus described, comprising the electrode 12 and at least a portion of the leads 14, may be easily implanted subcutaneously in a patient using the following procedure. A small incision (1.2–1.5 cm in length) is made in the skin of the patient in close proximity to the musculature desired to be stimulated. Using a blunt instrument a cavity is formed between the fatty layer 16 and the cural or deep fascia 18 (see FIG. 1). The electrode is inserted and deposited within the cavity by spatula-type forceps. Once the spatula is removed, a cannula is inserted from the location of the electrode to either the location of the skin where the leads are to exit the body or to an internal excitation source. The electrode leads are fed through the cannula to the outside of the body or the internal excitation source. The cannula is then removed and the small incision is sutured closed.

The electrode need not be sutured into position because the invention contemplates minor movement of the electrode with respect to the nerves or muscle fiber to be stimulated. The pressure at the interface of the fatty layer 16 and the cural or deep fascia 18 is sufficient to maintain the electrode 12 in proper position. This area of implantation is relatively unstressed, as compared to being directly on or in the muscle fiber. Thus, this relatively noninvasive surgery is performed superficial to the cural or deep fascia and the underlying nerves and arteries.

Minor movement of the electrode 12 with respect to the nerves or muscle fiber to be stimulated is tolerated because the fairly large surface area of the platinum sheet supports an amount of electrical charge sufficient to innervate a significant number of nerves or muscle fibers. Thus, the position of the electrode 12 need not be pinpointed to a critical degree of accuracy in order to provide effective recruitment of musculature.

Accordingly, the preferred embodiment of a system for electrically stimulating muscle fiber or for sensing the local electrical potential at its surface has been described. With the foregoing description in mind, however, it is understood that this description is made only by way of example, that the invention is not limited to the particular embodiments described herein, and that various rearrangements, modifications, and substitutions may be implemented without departing from the true spirit of the invention as hereinafter claimed.

What we claim is:

1. An implantable device for electrically stimulating skeletal musculature or sensing electrical potential, comprising:

an electrode subcutaneously implantable beneath the skin and physically separated from the skeletal musculature and nerves controlling the skeletal musculature, said electrode comprising a single sheet of electrically conductive material having a first surface adapted to face the skeletal musculature and an opposite surface adapted to face away from the skeletal musculature, said electrode defined by an outer perimetric edge;

a flexible casing comprising (i) a first layer of flexible biocompatible material adjacent to and substantially covering said opposite surface of said electrically conductive sheet, and (ii) a second layer of flexible biocompatible material covering a portion of said first surface of said electrode and provided with at least one central opening therein for exposing said first surface of said sheet of electrically conductive material, said electrically conductive sheet having a surface area sufficiently large to maintain a charge density of no more than 0.25 $\mu C/mm^2$ so as to prevent corrosion of the electrode and damage to surrounding tissue; and at least one electrical lead attached at one end to said electrically conductive sheet and attachable at an opposite end to an electrical current source.

2. The device of claim 1, wherein said at least one central opening is defined by a perimetric border, said perimetric border extending from said at least one central opening to said outer perimetric edge of said electrode and having no apertures therein.

3. The device of claim 2 wherein said electrode is implantable adjacent a fatty layer beneath the skin.

4. The device of claim 2, wherein said electrically conductive sheet is generally planar and is comprised of a noble metal.

5. The device of claim 4, wherein said generally planar electrically conductive sheet is comprised of platinum.

6. The device of claim 2, wherein said flexible casing further comprises a fabric mesh intermediate said second layer of flexible biocompatible material and said first surface of said electrically conductive sheet.

7. The device of claim 6, wherein said fabric mesh is constructed from polyethyleneterephthalate and said first and second layers of flexible biocompatible material are constructed from a silicone elastomer.

8. The device of claim 6, wherein at least said first surface of said electrically conductive sheet is coated with an oxide coating.

9. The device of claim 2, wherein said at least one electrical lead is attached at one end to said electrically conductive sheet by spot welding.

10. The device of claim 9, wherein said at least one electrical lead comprises a pair of electrical leads, each of said leads being wrapped generally in the form of a helix around a core.

11. The device of claim 10, wherein a portion of each of said helically wrapped leads is coiled, thereby forming a compound helical section.

12. The device of claim 11, wherein said electrical leads are formed of stranded stainless steel wire.

13. The device of claim 12, wherein said electrical leads comprise wire constructed from a cobalt alloy.

14. The device of claim 12, wherein said stainless steel wire is coated with polytetrafluoroethylene and wound around a flexible and biocompatible polypropylene core.

15. The device of claim 12, wherein at least a portion of each of the helically wound electrical leads are covered by flexible tubing.

16. A method of implanting within the body of a patient a device for electrically stimulating skeletal musculature or sensing electrical potential, said method comprising the steps of:

making an incision through the skin of the patient and through an underlying fatty layer;

forming a cavity between said fatty layer and a layer of fascia beneath the fatty layer;

depositing within said cavity an electrode comprising (i) a single sheet of electrically conductive material having a first surface adapted to face the skeletal musculature and an opposite surface adapted to face away from the skeletal musculature; (ii) a flexible casing covering at least a substantial portion of said opposite surface of said electrically conductive sheet; and (iii) at least one electrical lead attached at one end to said electrically conductive sheet and attachable at an opposite end to an electrical current source, such that said electrode remains physically separated from the musculature and nerves controlling the musculature; and at least partially closing said incision in the skin.

17. An implantable device for electrically stimulating skeletal musculature or sensing electrical potential, comprising:

an electrode subcutaneously implantable beneath the skin and physically separated from the skeletal musculature and nerves controlling the skeletal musculature, said electrode comprising a single sheet of electrically conductive material having a first surface adapted to face the skeletal musculature and an opposite surface adapted to face away from the skeletal musculature, said electrically conductive sheet having a surface area sufficiently large to maintain a charge density of less than 0.25 $\mu C/mm^2$ so as to prevent corrosion of the electrode and damage to surrounding tissue;

a flexible casing covering at least a substantial portion of said opposite surface of said electrically conductive sheet, said flexible casing comprising (i) a first layer of flexible biocompatible material of a thickness not to exceed 0.5 millimeter adjacent said opposite surface of said electrically conductive sheet, (ii) a second layer of flexible biocompatible material of a thickness not to exceed 0.5 millimeter surrounding a perimeter of said first surface of said electrically conductive sheet and (iii) a fabric mesh intermediate said second layer of flexible biocompatible material and said first surface of said electrically conductive sheet; and at least one electrical lead attached at one end to said electrically conductive sheet and attachable at an opposite end to an electrical current source.

* * * * *